United States Patent
Thomas et al.

(10) Patent No.: US 11,103,452 B2
(45) Date of Patent: Aug. 31, 2021

(54) TRAMADOL HYDROCHLORIDE SOLUTION

(71) Applicant: Athena Bioscience, LLC, Athens, GA (US)

(72) Inventors: H. Greg Thomas, Carrollton, GA (US); Richard LeVasseur, Oakwood, GA (US); Jeffrey S. Kiel, Gainesville, GA (US)

(73) Assignee: Athena Bioscience, LLC, Athens, GA (US)

( * ) Notice: Subject to any disclaimer, the term of this patent is extended or adjusted under 35 U.S.C. 154(b) by 0 days.

(21) Appl. No.: 17/009,565

(22) Filed: Sep. 1, 2020

(65) Prior Publication Data
US 2021/0137835 A1 May 13, 2021

Related U.S. Application Data

(60) Provisional application No. 62/932,963, filed on Nov. 8, 2019.

(51) Int. Cl.
*A61K 9/08* (2006.01)
*A61K 9/00* (2006.01)
*A61K 47/12* (2006.01)
*A61K 47/10* (2017.01)
*A61K 47/26* (2006.01)
*A61K 31/135* (2006.01)

(52) U.S. Cl.
CPC .............. *A61K 9/08* (2013.01); *A61K 9/0053* (2013.01); *A61K 31/135* (2013.01); *A61K 47/10* (2013.01); *A61K 47/12* (2013.01); *A61K 47/26* (2013.01)

(58) Field of Classification Search
CPC ...... A61K 9/08; A61K 9/0053; A61K 31/135; A61K 47/10; A61K 47/12; A61K 47/26
See application file for complete search history.

(56) References Cited

U.S. PATENT DOCUMENTS

| 6,339,105 B1 | 1/2002 | Kamin et al. |
| 2003/0118654 A1* | 6/2003 | Santos ................ A61K 9/0095 |
| | | 31/545 |
| 2009/0117191 A1 | 5/2009 | Brown Miller et al. |
| 2018/0140566 A1 | 5/2018 | Chen et al. |
| 2018/0228797 A1 | 8/2018 | Bosse et al. |
| 2019/0209529 A1 | 7/2019 | Nagar et al. |

FOREIGN PATENT DOCUMENTS

| WO | WO-2019161938 | 8/2019 | |
| WO | WO-2019174755 A1 * | 9/2019 | ............... A61K 9/08 |

OTHER PUBLICATIONS

ULTRAM® prescribing information, Oct. 2019.
Polonini et al., "Compatibility of cholecalciferol, haloperidol, imipramine hydrochloride, levodopa/carbidopa, lorazepam, minocycline hydrochloride, tacrolimus monohydrate, terbinafine, tramadol hydrochloride and valsartan in SrySpend® PH4 oral suspensions", *Pharmazie* (2016) 71(4):185-191.
Tramadol Hydrochloride, USP-NF, 2013.
Wagner et al., "Stability of oral liquid preparations of tramadol in strawberry syrup and a sugar-free vehicle", *Am. J. Health-Syst. Pharm.* (2003) 60(12): 1268-1270.
International Search Report issued in PCT/US2020/59441 dated Mar. 9, 2021.

* cited by examiner

*Primary Examiner* — Robert A Wax
*Assistant Examiner* — Olga V. Tcherkasskaya
(74) *Attorney, Agent, or Firm* — Blank Rome LLP

(57) ABSTRACT

Disclosed herein is an analgesic solution for the treatment of pain comprising a pain-relieving effective amount of tramadol or a pharmaceutically acceptable salt thereof, a method of treating pain by administering said analgesic solution to a subject in need thereof, a kit that includes containers of the analgesic solution, and a dosing regimen for the analgesic solution.

20 Claims, 3 Drawing Sheets

| 18 Day Titration Schedule Tramadol Oral Solution 25mg/5mL or 50mg/10mL | | |
|---|---|---|
| Day 1 | 1 X 25mg/5mL | a.m. |
| Day 2 | 1 X 25mg/5mL | a.m. |
| Day 3 | 1 X 25mg/5mL | a.m. |
| Day 4 | 2 X 25mg/5mL | b.i.d. |
| Day 5 | 2 X 25mg/5mL | b.i.d. |
| Day 6 | 2 X 25mg/5mL | b.i.d. |
| Day 7 | 3 X 25mg/5mL | t.i.d. |
| Day 8 | 3 X 25mg/5mL | t.i.d. |
| Day 9 | 3 X 25mg/5mL | t.i.d. |
| Day 10 | 4 X 25mg/5mL | q.i.d. |
| Day 11 | 4 X 25mg/5mL | q.i.d. |
| Day 12 | 4 X 25mg/5mL | q.i.d. |
| Day 13 | 3 X 50mg/10mL | t.i.d. |
| Day 14 | 3 X 50mg/10mL | t.i.d. |
| Day 15 | 3 X 50mg/10mL | t.i.d. |
| Day 16 | 4 X 50mg/10mL | q.i.d. |
| Day 17 | 4 X 50mg/10mL | q.i.d. |
| Day 18 | 4 X 50mg/10mL | q.i.d. |

FIG. 1

| 25 mg Dosing Card | | | | |
|---|---|---|---|---|
| Day 1 | 25mg/5mL | | | |
| Day 2 | 25mg/5mL | | | |
| Day 3 | 25mg/5mL | | | |
| Day 4 | 25mg/5mL | 25mg/5mL | | |
| Day 5 | 25mg/5mL | 25mg/5mL | | |
| Day 6 | 25mg/5mL | 25mg/5mL | | |
| Day 7 | 25mg/5mL | 25mg/5mL | 25mg/5mL | |
| Day 8 | 25mg/5mL | 25mg/5mL | 25mg/5mL | |
| Day 9 | 25mg/5mL | 25mg/5mL | 25mg/5mL | |
| Day 10 | 25mg/5mL | 25mg/5mL | 25mg/5mL | 25mg/5mL |
| Day 11 | 25mg/5mL | 25mg/5mL | 25mg/5mL | 25mg/5mL |
| Day 12 | 25mg/5mL | 25mg/5mL | 25mg/5mL | 25mg/5mL |
| 50 mg Dosing Card | | | | |
| Day 13 | 50mg/10mL | 50mg/10mL | 50mg/10mL | |
| Day 14 | 50mg/10mL | 50mg/10mL | 50mg/10mL | |
| Day 15 | 50mg/10mL | 50mg/10mL | 50mg/10mL | |
| Day 16 | 50mg/10mL | 50mg/10mL | 50mg/10mL | 50mg/10mL |
| Day 17 | 50mg/10mL | 50mg/10mL | 50mg/10mL | 50mg/10mL |
| Day 18 | 50mg/10mL | 50mg/10mL | 50mg/10mL | 50mg/10mL |

FIG. 2

TRAMADOL HYDROCHLORIDE SOLUTION

This application claims the benefit of U.S. Patent Application No. 62/932,963, filed Nov. 8, 2019, which is hereby incorporated by reference.

FIELD OF THE INVENTION

Disclosed herein is an oral analgesic solution for the treatment of pain comprising a pain-relieving effective amount of tramadol or a pharmaceutically acceptable salt thereof, a method of treating pain by administering said analgesic solution to a subject in need thereof, a kit that includes containers of the analgesic solution, and a dosing regimen for the analgesic solution.

BACKGROUND

Tramadol hydrochloride is referred to chemically as (±) cis-2-[(dimethylamino)methyl]-1-(3-methoxyphenyl)cyclohexan-1-ol, hydrochloride. Tramadol is an opioid agonist and inhibitor of norepinephrine and serotonin re-uptake. Opioid activity is due to both low affinity binding of tramadol and higher affinity binding of a tramadol metabolite (viz., 3-[cis-2-[(dimethylamino)methyl]-1-hydroxycyclohexyl]-phenol or O-desmethyltramadol (ODMT)) to μ-opioid receptors. In animal models, ODMT is up to 6 times more potent than tramadol in producing analgesia and 200 times more potent in μ-opioid binding. The relative contribution of both tramadol and ODMT to human analgesia is dependent upon the plasma concentrations of each compound.

Tramadol hydrochloride has been commercially available as immediate release tablets since 1995 under the brand name ULTRAM®. ULTRAM® tablets contain 50 mg of tramadol hydrochloride, together with inactive ingredients including: pregelatinized corn starch, modified starch (corn), hypromellose, lactose, magnesium stearate, microcrystalline cellulose, polyethylene glycol, polysorbate 80, sodium starch glycolate, titanium dioxide, and carnuba wax.

ULTRAM® is indicated in adults for the management of pain severe enough to require an opioid analgesic and for which alternative treatments are inadequate. Studies have shown that ULTRAM® is useful for the treatment of chronic pain in elderly patients associated with, for example, osteoarthritis and chronic low-back syndrome.

Some patients may experience dizziness, vertigo, nausea, and vomiting after ingesting ULTRAM® tablets. Accordingly, for patients not requiring rapid onset of analgesic effect, the tolerability of ULTRAM® can be improved by initiating therapy with a titration regimen. See, e.g., Kamin et al., Analgesic Regimen, U.S. Pat. No. 6,339,105 B1 ("Kamin"); see also the Prescribing Information for ULTRAM® (tramadol hydrochloride) tablets, for oral use, as of Oct. 7, 2019 ("ULTRAM® Label"). For instance, the ULTRAM® Label recommends starting ULTRAM® at 25 mg/day and titrated in 25 mg increments as separate doses every 3 days to reach 100 mg/day (25 mg four times a day). Thereafter the total daily dose may be increased by 50 mg as tolerated every 3 days to reach 200 mg/day (50 mg four times a day). After titration, ULTRAM® 50 to 100 mg can be administered as needed for pain relief every 4 to 6 hours not to exceed 400 mg/day.

A problem associated with the use of ULTRAM® and the recommended dose titration is the necessity to break scored tablets. And a further complication is that generic equivalents of ULTRAM® are not scored. Having to break a scored/unscored tablet may be problematic in that an irregular break may result in incorrect dosing. This also may be problematic insofar that tramadol hydrochloride has a bitter taste, thereby, resulting in patient non-compliance. And a separate problem that is unrelated to the recommended dose titration is that ULTRAM® is prescribed typically to elderly patients (e.g., for the relief of pain associated with osteoarthritis). It is generally recognized that many elderly people will encounter difficulties swallowing conventional oral dosage forms, including tablets. See, e.g., Chang et al., Fast-Dissolving Tablets, Pharm. Tech. (2000) 24: 52-58 ("Chang"). Accordingly, ULTRAM® may be unsuitable for many elderly patients because said patients may encounter problems swallowing a tablet.

Extemporaneous tramadol preparations are known. See, e.g., Wagner et al., Stability of oral liquid preparations of tramadol in strawberry syrup and a sugar-free vehicle, Am. J. Health-Syst. Pharm. (2003) 60(12): 1268-1270 ("Wagner") and Polonini et al., Compatibility of cholecalciferol, haloperidol, imipramine hydrochloride, levodopa/carbidopa, lorazepam, minocycline hydrochloride, tacrolimus monohydrate, terbinafine, tramadol hydrochloride and valsartan in SrySpend® PH4 oral suspensions, Pharmazie (2016) 71(4): 185-191 ("Polonini"). Wagner describes preparing an oral suspension of tramadol hydrochloride by crushing ULTRAM® tablets and suspending the crushed powder in one of two vehicles (viz., either ORA-SWEET® SF or ORA-PLUS® and strawberry syrup). Wagner states that the extemporaneous prepared suspension should include a label stating "Shake Well Before Use," and recommends mixing the suspension with chocolate syrup before administration to mask the bitter aftertaste. Polonini describes preparing an oral suspension by compounding tramadol hydrochloride using SyrSpend® SF PH4 (pH 4.2). Based on data presented therein, Polonini states that the beyond-use date of the preparation was found to be at least 90 days both at refrigerated and at room temperature. It is generally recognized that extemporaneously prepared suspensions may suffer numerous problems, including, for example, poor taste, inadequate content uniformity, limited shelf-life, the possibility of microbial contamination, use of unapproved container/closure, poor taste, among others. And as related to an opioid agonist, such as tramadol, extemporaneously prepared suspensions may give rise to calculation and measurement errors may lead to an overdosed patient, which may lead to seizure and respiratory depression.

The analgesic solution disclosed and claimed herein is meant to overcome the shortcomings of the ULTRAM® tablets for oral use, as well as known extemporaneously prepared oral suspensions.

US 2018/0140566 describes acetaminophen and tramadol compound oral solution in a solvent system comprising polyethylene glycol.

WO 2019/161938 describes an oral pharmaceutical solution comprising tramadol or a pharmaceutically acceptable salt thereof in a concentration of 10 mg/mL to 40 mg/mL. It was observed that more dilute solutions, which required larger volumes to be administered, resulted in a longer lasting intense bitter aftertaste. WO 2019/161938 further teaches that the relatively high concentrations of taste masking agents that are necessary for masking the bitterness of tramadol hydrochloride at a concentration below 10 mg/mL, such as 8 mg/ml, cause a negative effect on solubility, resulting in the formation of a suspension with the presence of visible particles that become apparent upon production, and still exhibited a disagreeable sweet aftertaste.

Furthermore, more dilute drug solutions typically degrade faster than more concentrated solutions and require larger doses, which may be more distasteful for less palatable drugs.

SUMMARY OF THE INVENTION

The present inventors have discovered that a low concentration solution of tramadol hydrochloride (for example, at 5 mg/mL) can be prepared which is stable and does not exhibit the intense bitter aftertaste common to tramadol solutions.

One aspect is an aqueous oral analgesic solution comprising:
(a) from about 4.5 to about 5.5 mg/mL (preferably about 5 mg/mL) of tramadol hydrochloride as the sole active ingredient;
(b) from about 4 to about 10% w/v of propylene glycol;
(c) from about 10 to about 30% w/v of glycerin;
(d) a sufficient amount of a buffer to maintain the pH of the oral solution from about 4.5 to about 5.5;
(e) from about 0.01% to about 0.2% sucralose;
(f) a flavoring agent in an amount of from about 0.1% w/v to about 1% or 5% w/v;
(g) sodium benzoate in an amount of from about 0.1% w/v to about 1% w/v; and
(h) a sufficient amount of water.

In one embodiment, the amount of propylene glycol ranges from about 5 to about 7% w/v. The buffer can be a citrate buffer, such as a mixture of citric acid and trisodium citrate. The citrate buffer can be present in an amount of from about 0.2% w/v to about 0.4% w/v. The sucralose can be present in an amount of about 0.1% w/v. The flavoring agent, which can be grape flavor, can be present in an amount of from about 0.2% w/v to about 0.4% w/v. The sodium benzoate can be present in an amount of from about 0.3% w/v to about 0.4% w/v.

Another aspect is an aqueous oral analgesic solution comprising:
(a) about 5 mg/mL of tramadol hydrochloride as the sole active ingredient;
(b) about 5% w/v of propylene glycol;
(c) about 20% w/v of glycerin;
(d) about 0.1% w/v of citric acid and about 0.2% w/v of trisodium citrate dihydrate;
(e) about 0.07% w/v of sucralose;
(f) a flavoring agent in an amount of from about 0.1% w/v to about 1% w/v;
(g) about 0.375% w/v of sodium benzoate; and
(h) water,
wherein the solution has a pH of from about 4.5 to about 5.5.

In one embodiment of any of the oral solutions described herein, the pH of the oral solution ranges from about 4.8 to about 5.4. In another embodiment, the pH is 5.0 or 5.1.

In one embodiment of any of the oral solutions described herein, the solution does not contain any active pharmaceutical ingredients other than tramadol hydrochloride.

In one embodiment of any of the oral solutions described herein, the oral solution is free or substantially free of (i) sugars (such as sucrose), (ii) parabens (such as methylparaben or propylparaben), (iii) non-ionic surfactants and/or co-solvents (such as castor oil, modified castor oil, ethanol, polyethylene glycol, povidone, copovidone, and sorbitan monolaurate), (iv) mint oil, (v) aniseed flavor, (vi) saccharin and salts thereof (such as sodium saccharin), (vii) sodium cyclamate, (viii) polyoxyl 40 hydrogenated castor oil, and (ix) any combination of any of the foregoing.

Another aspect of the present invention is an oral analgesic solution for the treatment of pain comprising: (a) tramadol or a pharmaceutically acceptable salt thereof in an amount of from about 0.1% w/v to about 2.5% w/v; (b) a non-aqueous solvent in an amount of from about 0 to about 30% w/v; (c) a taste enhancer in an amount of from about 0% w/v to 30% w/v; (d) a sufficient amount of a buffer to maintain the pH of the oral solution from about 3 to about 7; (e) a sweetener in an amount of from about 0.01% w/v to about 1.0% w/v; (f) a flavoring agent in an amount of from about 0.1% w/v to about 5% w/v; (g) a preservative in an amount of from about 0% w/v to about 4% w/v; (h) optionally, a pH adjusting agent; and (i) a sufficient amount of water.

Yet another aspect is a method of treating pain in a patient in need thereof comprising administering an effective amount of an analgesic solution as described herein.

Yet another aspect is a method of treating a patient (e.g., an adult patient) having pain severe enough to require an opioid analgesic and for which alternative treatments are inadequate. The method comprises administering an effective amount of an analgesic solution as described herein.

In the methods described herein, for patients not requiring rapid onset of analgesic effect, the tolerability of the analgesic solution can be improved by initiating therapy with the following titration regimen: Start administering the analgesic solution in a sufficient amount to provide 25 mg per day of tramadol or a pharmaceutically acceptable salt thereof (e.g., tramadol hydrochloride) and titrated in 25 mg increments as separate doses every 3 days to reach 100 mg per day (25 mg four times a day). Thereafter, the total daily dose may be increased by 50 mg per day as tolerated every 3 days to reach 200 mg per day (50 mg four times a day). After titration, 50 to 100 mg can be administered as needed for pain relief every 4 to 6 hours not to exceed 400 mg per day.

For patients for whom rapid onset of analgesic effect is required and for whom the benefits outweigh the risk of discontinuation due to adverse events associated with higher initial doses, the analgesic solution in a sufficient amount to provide 50 to 100 mg per day of tramadol or a pharmaceutically acceptable salt thereof (e.g., tramadol hydrochloride) can be administered as needed for pain relief every four to six hours, not to exceed 400 mg per day.

Definitions/Abbreviations

The phrase "a" or "an" entity as used herein refers to one or more of that entity. For example, an agent refers to one or more agents or at least one agent. As such, the terms "a" (or "an"), "one or more", and "at least one" can be used interchangeably herein. The use of the definite article ("the") to refer to "an entity" refers to one or more of that entity. For example, when the expression "the agent" refers to the previously recitation of "an agent" it is understood that the expression "the agent" refers to one or more agents.

The term "about" has its customary meaning, as defined in the USP, Section 8.20, which states that "about" indicates a quantity within 10%.

A stated amount for a compositional ingredient that is not preceded by the term "about" does not mean that there is no variance for the stated term, as one of ordinary skill would understand that there is always some possibility of a degree of variability generally associated with experimental error.

The concentration unit "% w/v" is a measure of the weight amount of a specified ingredient based on the total volume of the composition.

As used herein, "substantially free" of a material may refer to an oral solution where the material is present in an amount of less than 0.2% w/v, less than 0.1% w/v, less than 0.02% w/v, or less than 0.01% w/v in the oral solution.

The terms "optional" or "optionally" as used herein means that a subsequently described event or circumstance may but need not occur, and that the description includes instances where the event or circumstance occurs and instances in which it does not.

The term "administration" or "administered" or "administering" as used herein refers to administration of a unit dose of a composition described herein to a subject. The unit dose may be administered over repeated time intervals, as needed.

q.d. (quaque die) means one a day.
b.i.d. (bis in die) means two times a day.
t.i.d. (ter in die) means three times a day.
q.i.d. (quater in die) means four times a day.
$T_{max}$ refers to the observed time to reach a maximum plasma concentration.
$C_{max}$ refers to the maximum plasma concentration.
$AUC_{0-inf}$ refers to the area under the curve in a plot of analyte concentration in blood plasma versus time from zero to infinity.
$AUC_{0-t}$ refers to the area under the curve in a plot of analyte concentration in blood plasma versus time from zero to a specified time.
$t_{1/2}$ refers to the time required to eliminate one-half of the plasma concentration of an analyte.
Kel refers to the elimination rate constant.
ODMT means O-desmethyl-tramadol.

The expression "immediate release composition comprising tramadol" as used herein refers to ULTRAM® (tramadol hydrochloride) 50 mg tablet (U.S. New Drug Application No. 020281), for oral use, which is alternatively referred to herein as Reference Product or RLD. ULTRAM® tablets contain 50 mg of tramadol hydrochloride and are white in color. Inactive ingredients in the tablet are pregelatinized corn starch, modified starch (corn), hypromellose, lactose, magnesium stearate, microcrystalline cellulose, polyethylene glycol, polysorbate 80, sodium starch glycolate, titanium dioxide and carnauba wax.

The terms "bioequivalence," "bioequivalency," or "bioequivalent," as used herein is established by observing:
a) a 90% Confidence Interval between 80% and 125% for the ratio (of Test Product vs. Reference Product) of the geometric mean of $AUC_{0-t}$ of tramadol and/or ODMT;
b) a 90% Confidence Interval between 80% and 125% for the ratio (of Test Product vs. Reference Product) of the geometric mean $AUC_{0-inf}$ of tramadol and/or ODMT;
c) a 90% Confidence Interval between 80% and 125% for the ratio (of Test Product vs Reference Product) of the geometric mean $C_{max}$ of tramadol and/or ODMT; or
d) a combination of any of a) to c).

The pharmaceutically acceptable salts of tramadol, as described herein, are acid addition salts wherein acid is selected from hydrochloric acid, hydrobromic acid, embonic acid, (2S,3S)-dibenzoyltartaric acid, dibenzoyltartaric acid, sebacic acid, 1-hydroxy-naphthoic acid, phosphoric acid, L-(+)-tartaric acid, lysinic acid, L-lysinic acid, D-(+)-malic acid, 4-methylbenzenesulfonic acid, ethanesulfonic acid, benzoic acid, cinnamic acid, L-(+)-lactic acid, S-(+)-mandelic acid, (+)-camphor-10-sulfonic acid, gluconic acid, L-(+)-ascorbic acid, ascorbic acid, palmitic acid, naphthalene-1,5-disulfonic acid, hexanoic acid, oleic acid, stearic acid, gentisic acid, octanoic acid, decanoic acid, nitric acid, orotic acid, mucic acid, alginic acid and acesulfamic acid, nicotinic acid, hydrogen bromide, sulfuric acid, acetic acid, propionic acid, oxalic acid, succinic acid, fumaric acid, maleic acid, hippuric acid, lactic acid, mandelic acid, malonic acid, malic acid, tartaric acid, methanesulfonic acid, citric acid, lactic acid. Preferably hydrochloric acid addition salt of tramadol is used for oral solutions described herein.

BRIEF DESCRIPTIONS OF THE DRAWINGS

FIG. 1 represents an 18 Day Titration Schedule for Tramadol Oral Solution of 25 mg/5 mL or 50 mg/10 mL (viz., 5 mg/mL based on tramadol hydrochloride).

FIG. 2 represents an exemplary 18 Day Dosing Card for Tramadol Oral Solution of 25 mg/5 mL or 50 mg/10 mL (viz., 5 mg/mL based on tramadol hydrochloride).

DETAILED DESCRIPTION

Figure 3:
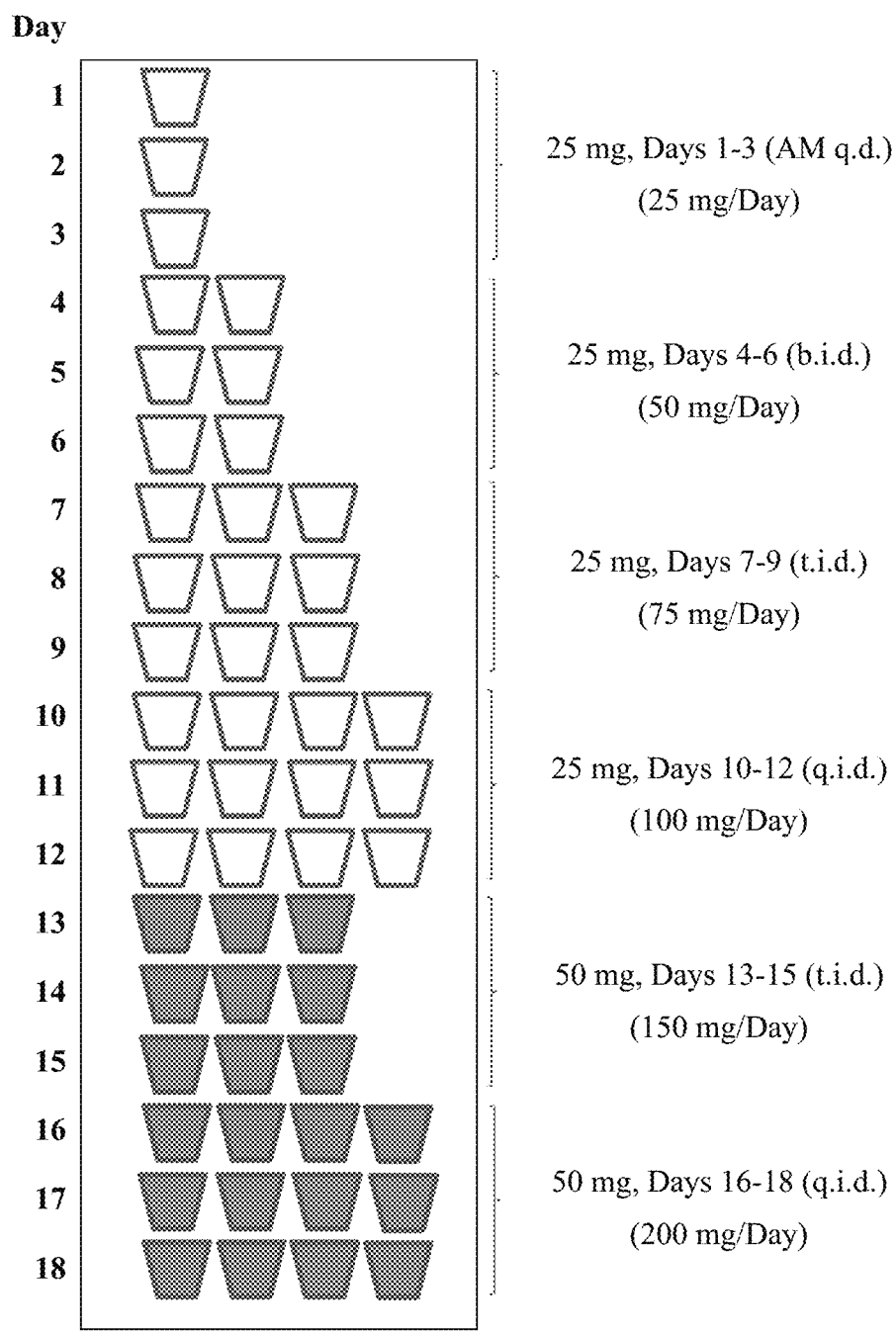
FIG. 3 represents an exemplary 18 Day Dosing Card for Tramadol Oral Solution of 25 mg/5 mL or 50 mg/10 mL (viz., 5 mg/mL based on tramadol hydrochloride).

The information that follows details various embodiments of the disclosure. For the avoidance of doubt, it is specifically intended that any particular feature(s) described individually in any one of these paragraphs (or part thereof) may be combined with one or more other features described in one or more of the remaining paragraphs (or part thereof). In other words, it is explicitly intended that the features described below individually in each paragraph (or part thereof) represent aspects of the disclosure that may be taken in isolation and/or combined with other aspects of the disclosure. The skilled person will appreciate that the claimed subject matter extends to such combinations of features and that these have not been recited in detail here in the interests of brevity.

Oral Analgesic Solution

One embodiment is an oral analgesic solution for the treatment of pain comprising: (a) tramadol or a pharmaceutically acceptable salt thereof in an amount of from about 0.1% w/v to about 2.5% w/v; (b) a non-aqueous solvent in an amount of from about 0 to about 30% w/v; (c) a taste enhancer in an amount of from about 0% w/v to 30% w/v; (d) a sufficient amount of a buffer to maintain the pH of the oral solution from about 3 to about 7; (e) a sweetener in an amount of from about 0.01% w/v to about 1.0% w/v; (f) a flavoring agent in an amount of from about 0.1% w/v to about 5% w/v; (g) a preservative in an amount of from about 0% w/v to about 4% w/v; (h) optionally, a pH adjusting agent; and (i) a sufficient amount of water.

In any one of the aspects disclosed herein, a sufficient amount of water (water refers to USP rated purified water that satisfies the USP requirements for Purified Water, e.g., <643> for total organic carbon and <645> for water conductivity).

In any one of the aspects disclosed herein, the solution is free or substantially free of polyethylene glycol.

In any one of the aspects disclosed herein, the sole active ingredient in the solution is tramadol hydrochloride.

In one embodiment, the tramadol or a pharmaceutically acceptable salt thereof (a) comprises tramadol hydrochloride in an amount of from about 0.45% w/v to about 0.55% w/v; the non-aqueous solvent (b) is present an amount of from about 0% w/v to about 10% w/v; the taste enhancer (c) is present in an amount of from about 0% w/v to 30% w/v; the buffer (d) is present in an amount of from about 0.20% w/v to about 0.40% w/v; the sweetener (e) is present in an amount of from about 0.01% w/v to about 0.1%; the flavoring agent (f) is present in an amount of from about 0.2% w/v to about 0.4% w/v; and the preservative (g) is present in an amount of from about 0.2% w/v to about 0.4% w/v.

In another embodiment, the tramadol or a pharmaceutically acceptable salt thereof (a) comprises tramadol hydrochloride in an amount of from about 0.45% w/v to about 0.55% w/v; the non-aqueous solvent (b) is present an amount from about 2% w/v to about 8% w/v; the taste enhancer (c) is present in an amount of from about 10% w/v to about 30% w/v; the buffer (d) is present in an amount of from about 0.2% w/v to about 0.4% w/v; the sweetener (e) is present in an amount of about 0.01% w/v; the flavoring agent (f) is present in an amount of from about 0.2% w/v to about 0.4% w/v; and the preservative (g) is present in an amount of from about 0.3% w/v to about 0.4% w/v.

One may appreciate that the buffer may be a pharmaceutically acceptable buffer capable of obtaining a pH of the analgesic solution described herein. Examples of buffers include, but are not limited to maleic acid, tartaric acid, lactic acid, citric acid, acetic acid, sodium bicarbonate, sodium phosphate, or a combination thereof. In one aspect, the buffer may be a citrate buffer.

In another embodiment, the tramadol or a pharmaceutically acceptable salt thereof (a) comprises tramadol hydrochloride in an amount of from about 0.45% w/v to about 0.55% w/v; the non-aqueous solvent (b) comprises propylene glycol in an amount of from about 2% w/v to about 8% w/v; the taste enhancer (c) comprises glycerin in an amount of from about 10% w/v to about 30% w/v; the buffer (d) comprises a citrate buffer present in an amount of from about 0.2% w/v to about 0.4% w/v; the sweetener (e) comprises sucralose present in an amount of about 0.01% w/v; the flavoring agent (f) comprises a grape flavor present in an amount of from about 0.2% w/v to about 0.4% w/v; and the preservative (g) comprises sodium benzoate in an amount of from about 0.3% w/v to about 0.4% w/v.

In yet another embodiment, the tramadol or a pharmaceutically acceptable salt thereof (a) comprises tramadol hydrochloride in an amount of from about 0.45% w/v to about 0.55% w/v; the non-aqueous solvent (b) comprises propylene glycol in an amount of about 5% w/v; the taste enhancer (c) comprises glycerin in an amount of about 20% w/v; the buffer (d) comprises a citrate buffer present in an amount of about 0.3% w/v; the sweetener (e) comprises sucralose present in an amount of about 0.01% w/v; the flavoring agent (f) comprises a grape flavor present in an amount of about 0.3% w/v; and the preservative (g) comprises sodium benzoate in an amount of about 0.375% w/v; and wherein the solution has a pH of from about 4.5 to about 5.5.

In yet another embodiment, the tramadol or a pharmaceutically acceptable salt thereof (a) comprises tramadol hydrochloride in an amount of from about 0.45% w/v to about 0.55% w/v; the non-aqueous solvent (b) comprises propylene glycol in an amount of about 5% w/v; the taste enhancer (c) comprises glycerin in an amount of about 20% w/v; the buffer (d) comprises a citrate buffer present in an amount of about 0.3% w/v; the sweetener (e) comprises sucralose present in an amount of about 0.07% w/v; the flavoring agent (f) comprises a grape flavor present in an amount of about 0.3% w/v; and the preservative (g) comprises sodium benzoate in an amount of about 0.375% w/v; and wherein the solution has a pH of from about 4.8 to about 5.4.

In a particular embodiment of any of the solutions described herein, the analgesic solution has a pH of about 5, or about 5.1.

In one embodiment of any of the solutions described herein, the solution exhibits an amount of tramadol hydrochloride of from about 0.45% w/v to about 0.55% w/v after storage at 25±2° C. and 40±5% relative humidity (RH) in a container for 24 months.

In another embodiment of any of the solutions described herein, the solution exhibits an amount of tramadol hydrochloride of from about 0.48% w/v to about 0.53% w/v after storage at 25±2° C. and 40±5% relative humidity in a container for 24 months.

In yet another embodiment of any of the solutions described herein, the solution exhibits an amount of tramadol hydrochloride of from about 0.49% w/v to about 0.51% w/v after storage at 25±2° C. and 40±5% relative humidity in a container for 24 months.

In yet another embodiment of any of the solutions described herein, the solution exhibits an amount of tramadol hydrochloride having a purity of at least 99.4% by HPLC after storage at 25±2° C. and 40±5% relative humidity in a container for 24 months.

In yet another aspect, a packaged oral solution as described herein exhibits a tramadol hydrochloride assay amount of at least 99.4% after a 24 month period while stored at 25±2° C. and 40±5% relative humidity.

A further aspect relates to a packaged oral solution as described herein having an amount of either Compound A or Compound B of not more than 0.20% by HPLC after a 24 month period while stored at 25±2° C. and 40±5% relative humidity.

A further aspect relates to a packaged analgesic solution of Aspect 5 or Aspect 6 having an amount of total impurities (e.g., Compounds A, B, C, D, and/or E) of not more than 1.0% by HPLC after a 24 month period while stored at 25±2° C. and 40±5% relative humidity.

In one embodiment of any of the oral solutions described herein, the solution is bioequivalent to an immediate release tablet composition (such as 50 mg ULTRAM® tablets, NDA No. 020281) comprising tramadol when administered to an adult human under fasted conditions.

In one embodiment of any of the oral solutions described herein, the solution is bioequivalent to an immediate release tablet composition comprising tramadol when administered to an adult human under fed conditions.

Based on bioequivalence testing conducted on human subjects, observed pharmacokinetic ("PK") data (e.g., were measured for tramadol and O-desmethyl-tramadol ("ODMT")) under fasted and fed conditions. The observed PK data from the bioequivalence testing were: (i) Cmax (tramadol, fasted): 170±50 ng/mL; AUC0-inf (tramadol, fasted): 1635±810 ng/mL; (ii) Cmax (ODMT, fasted): 47±23 ng/mL; AUC0-inf (ODMT, fasted): 644±275 hr*ng/mL; (iii) Cmax (tramadol, fed): 170±50 ng/mL; AUC0-inf (tramadol, fed): 1635±810 ng/mL; and (iv) Cmax (ODMT, fed): 47±23 hr*ng/mL; AUC0-inf (ODMT, fed): 644±275 hr*ng/mL.

In one embodiment of any of the oral solutions described herein, the solution exhibits a tramadol Cmax of from about 120 ng/mL to about 220 ng/mL and an O-desmethyltramadol Cmax of from about 24 ng/mL to about 70 ng/mL following administration of the solution to an adult human under fasted conditions. In one embodiment, the solution is bioequivalent to an immediate release tablet composition comprising tramadol when administered to an adult human under fasted conditions.

In one embodiment of any of the oral solutions described herein, the solution exhibits a tramadol AUC0-inf of from about 825 hr*ng/mL to about 2445 hr*ng/mL and an 0-desmethyltramadol AUC0-inf of from about 370 hr*ng/mL to about 920 hr*ng/mL following administration of the solution to an adult human under fasted conditions. In one embodiment, the solution is bioequivalent to an immediate release tablet composition comprising tramadol when administered to an adult human under fasted conditions.

Yet another embodiment is a process for preparing the oral solution as described herein by a process substantially as described herein. In one embodiment, the process comprises adding ingredients (a) through (g), and a first suitable amount of water to a suitable vessel to obtain a first solution, optionally adjusting the pH of the first solution to a pH of about 3.1 with a suitable amount of aqueous hydrochloric acid, and adding a second suitable amount of water to the optionally pH-adjusted solution.

One embodiment is an analgesic solution prepared by this process.

Yet another embodiment is a method of treating pain in a subject in need thereof, which comprises administering to the subject an effective amount of the analgesic solution of any one of an oral solution described herein.

Studies have shown that ULTRAM® is useful for the treatment of chronic pain in elderly human patients associated with, for example, osteoarthritis and chronic low-back syndrome. Thus, aspects contemplated herein relate to a method for the treatment of one of osteoarthritis and chronic low-back syndrome.

Kit and Dosing Regimen

As stated elsewhere, the analgesic solution may be packaged in a pharmaceutically acceptable container wherein the analgesic solution is packaged with a volume that ranges from about 5 mL to about 100 mL, including all volume amounts in between, such as, for example, about 10 mL, about 15 mL, about 20 mL, about 25 mL, about 30 mL, about 35 mL, about 40 mL, about 45 mL, about 50 mL, about 55 mL, about 60 mL, about 65 mL, about 70 mL, about 75 mL, about 80 mL, about 85 mL, about 90 mL, and about 90 mL.

In certain instances, it may be advantageous to package the analgesic solution disclosed herein in a volume of about 5 mL or about 10 mL. For example, an analgesic solution comprising tramadol or a pharmaceutically acceptable salt thereof having an amount of tramadol (based on the hydrochloride salt) of about 5 mg/mL permits administration of a dosage amount of tramadol, e.g., 25 mg (for a volume of about 5 mL) or 50 mg (for a volume of about 10 mL). For instance, an analgesic solution comprising about 5 mg/mL tramadol hydrochloride permits administration of a dosage amount of tramadol, e.g., 25 mg (for a volume of about 5 mL) or 50 mg (for a volume of about 10 mL).

The package may be in a suitable form acceptable to the end-user, including, for example, a cup, a vial, or a stick, each of which may be sealed to prevent spillage of the analgesic solution and to minimize introduction of an external contaminant. The container and, if applicable, its components, may comprise a pharmaceutically acceptable plastic. Further aspects disclosed herein relate to a kit.

A cup having a volume of about 7 mL may be used for a dosage volume of about 5 mL, while a cup having a volume of about 15 mL may be used for a dosage volume of about 10 mL.

The package, such as, a cup, may comprise a pharmaceutically acceptable plastic, including, for example, a high density polyethylene ("HDPE"), a low density polyethylene ("LDPE"), a linear low density polyethylene ("LLDPE"), a polypropylene ("PP"), a vulcanized thermoplastic ("TPV") comprised of a PP and an ethylene propylene diene monomer rubber ("EDPM"), a polyethylene copolymer, or a combination thereof. In one aspect, the package, such as a cup, comprises a HDPE.

The package, such as, a cup, may further comprise a colorant, for example, an amber colorant such as that described in DMF No. 33315 held by Polyone Corp, related to CC10292873XX (or Amber PE, CC10292873). In another aspect, the package, such as a cup, comprises a HDPE and an amber colorant having a light transmission of not more than 10% between 290 and 450 nm, measured according to USP <671>.

In one aspect, the cup has a volume of about 15 mL capable of holding a volume (e.g., about 10 mL) of an analgesic solution described herein. The cup has an outer diameter (top) that ranges from about 1.99 to about 2.02 inches (as measured by a micrometer).

In another aspect, the cup has a volume of about 7 mL capable of holding a volume (e.g., about 5 mL) of an analgesic solution described herein.

Cups described containing an analgesic solution described herein comprise a removable cup liner adhered thereto. For a cup having volume of about 17 mL, the removable liner has a width of about 2.5 inches (as measured by a micrometer) and comprises a pharmaceutically acceptable polymeric material, such as, for example a polyethylene terephthalate, which complies with USP <197> and USP <661>. One may appreciate that the cup liner adhesive comprises a pharmaceutically acceptable adhesive, including, for example, an adhesive comprising poly(ethylene-vinyl acetate), which complies with USP <197> and USP <661>.

One embodiment is a kit comprising a container that comprises the analgesic solution of any embodiment described herein and a written material describing the use of the packaged analgesic solution for the treatment of pain in a subject.

In one embodiment, the container comprises a volume of the analgesic solution of about 5 mL or about 10 mL.

In another embodiment, the container is a cup having a volume of about 7 mL or about 15 mL.

In yet another embodiment, the cup has a volume of about 7 mL and said cup comprises a HDPE and an amber colorant, said cup having a light transmission of not more than 10% between 290 and 450 nm, measured according to USP <671>.

In yet another embodiment, the cup has a volume of about 15 mL and said cup comprises a HDPE and an amber colorant, said cup having a light transmission of not more than 10% between 290 and 450 nm, measured according to USP <671>.

In another aspect related to the kit-container, the solution exhibits an amount of tramadol hydrochloride of from about 0.45% w/v to about 0.55% w/v after storage at 25±2° C. and 40±5% relative humidity after storage in a container for 24 months.

In yet another aspect related to the kit-container, the solution exhibits an amount of tramadol hydrochloride of from about 0.48% w/v to about 0.53% w/v after storage at 25±2° C. and 40±5% relative humidity after storage in a container for 24 months.

In a further aspect, the kit-container comprises about 5 mL or about 10 mL of the analgesic solution of any embodiment described herein and the solution exhibits an amount of tramadol hydrochloride of from about 0.49% w/v to about 0.51% w/v after storage at 25±2° C. and 40±5% relative humidity after storage in a container for 24 months.

In another aspect, the kit-container comprises about 5 mL or about 10 mL of the analgesic solution of any embodiment described herein and the amount of tramadol hydrochloride has a purity of at least 99.4% by HPLC after storage at 25±2° C. and 40±5% relative humidity after storage in the kit-container for 24 months.

In an additional aspect, the kit-container comprises about 5 mL or about 10 mL of the analgesic solution of any embodiment described herein and the tramadol hydrochloride assay amount of at least 99.4% after a 24 month period while stored at 25±2° C. and 40±5% relative humidity.

In another aspect, the kit-container comprises about 5 mL or about 10 mL of the analgesic solution of any embodiment described herein having an amount of either Compound A or Compound B of not more than 0.20% by HPLC after a 24 month period while stored at 25±2° C. and 40±5% relative humidity. In yet a further aspect, the kit-container comprises about 5 mL or about 10 mL of the analgesic solution of any embodiment described herein having an amount of total impurities (e.g., Compounds A, B, C, D, and/or E) of not more than 1.0% by HPLC after a 24 month period while stored at 25±2° C. and 40±5% relative humidity.

In one embodiment, the written material includes a dosing regimen substantially as described in any one of FIGS. 1-3. Although FIG. 3 depicts what might be referred to as a "cup," it is contemplated herein that the "cup" image may be a vial, a stick, or another pharmaceutically acceptable container.

Again, studies have shown that ULTRAM® is useful for the treatment of chronic pain in elderly human patients associated with, for example, osteoarthritis and chronic low-back syndrome. Thus, the written material may further comprise instructions to treat at least one of osteoarthritis and chronic low-back syndrome.

Yet another embodiment is a regimen for the treatment of pain, which comprises administering a subject in need thereof, about 25 mg of tramadol hydrochloride on days 1-3; about 50 mg of tramadol hydrochloride on days 4-6; about 75 mg of tramadol hydrochloride on days 7-9; about 100 mg of tramadol hydrochloride on days 10-12; about 150 mg of tramadol on days 13-15; and about 200 mg of tramadol hydrochloride on days 16-28 and thereafter, in the form of an analgesic solution of any embodiment described herein, whereby discontinuations due to adverse side effects are reduced.

Yet another embodiment is a regimen for the treatment of pain, which comprises administering to subject in need thereof about 25 mg of tramadol hydrochloride on days 1-3; about 50 mg of tramadol hydrochloride on days 4-6; about 75 mg of tramadol hydrochloride on days 7-9; about 100 mg of tramadol hydrochloride on days 10-12; about 150 mg of tramadol hydrochloride on days 13-15; and about 200 mg of tramadol hydrochloride on day 16 and thereafter, in the form of an analgesic solution of any embodiment described herein, whereby discontinuations due to adverse side effects are reduced.

Yet another embodiment is a regimen for the treatment of pain according which comprises administering to subject in need thereof about 25 mg of tramadol hydrochloride q.d. on days 1-3, about 25 of mg of tramadol hydrochloride b.i.d. on days 4-6, about 25 mg of tramadol hydrochloride t.i.d. on days 7-9, about 25 mg of tramadol hydrochloride q.i.d. on days 10-12, and about 50 mg of tramadol hydrochloride t.i.d. on days 13-28 in the form of the analgesic solution of any embodiment described herein, whereby discontinuations due to adverse side effects are reduced.

Again, studies have shown that ULTRAM® is useful for the treatment of chronic pain in elderly human patients associated with, for example, osteoarthritis and chronic low-back syndrome. Thus, aspects contemplated herein relate to a method for the treatment of one of osteoarthritis and chronic low-back syndrome.

And in one aspect, the analgesic solution disclosed herein may be applicable for the treatment of pain in a veterinary setting (e.g., use in dog and/or cats). Generally, a dose of tramadol (e.g., tramadol hydrochloride) in a veterinary setting ranges from about 1 to about 4 mg/kg, administered b.i.d., t.i.d., or in certain instances q.i.d.

One will appreciate that, where applicable, the expression "comprising" may be replaced by expression "consisting of" or "consisting essentially of" without departing from the information disclosed herein.

EXAMPLES

The analgesic solutions described herein was characterized by numerous tests, including: appearance; pH, USP <791>; Weight Loss ("Wt. Loss"), USP <671>; anti-microbial effectiveness testing, USP <51>; microbiological examination, USP <61>; and USP <62>, and specific gravity/density, USP <841>, Method I. Additionally, high performance liquid chromatography analysis, see generally, USP <621>, was performed on the analgesic solutions described herein for the following observables: Tramadol Hydrochloride Assay, Sodium Benzoate ("SB") Assay, Unspecified and Unidentified Impurities ("UU Imps."), and Total Impurities ("Total Imps."). Suitable HPLC methods include those described in Kartinasari et al., HPLC Determination and Validation of Tramadol Hydrochloride in Capsules, J. Liq. Chromat Related Tech. (2004) 27(4):737-744 ("Kartinasari") or Tramadol Hydrochloride, USP-NF, 2013 ("Tramadol HCl USP"). Assay and impurities may be identified and/or calculated from the HPLC results, as described in, for example, Bleisner, D. M., "Appendix V: Template for An Example Standard Test Method," in Validating Chromatographic Methods A Practical Guide, Wiley-Interscience, 2006, pp. 159-168 (doi:10.1002/0470042206.app5) ("Bleisner") and Venkanna et al., Synthesis of related substances of Tramadol hydrochloride, analgesic drug, J. Chem. Pharm. Res. (2014) 4(10): 4506-4513 ("Venkanna").

A substantial amount of development work was undertaken to achieve the solutions disclosed and claimed herein. Table 1 represents a summary of seven exemplary solutions.

TABLE 1

Summary of tramadol hydrochloride oral solutions

| Ingredient | Example 1 | 2 | 3 | 4 | 5 | 6 | 7 |
|---|---|---|---|---|---|---|---|
| | Ingredient Amounts, % w/v | | | | | | |
| Tramadol HCl USP | 0.50 | 0.50 | 0.50 | 0.50 | 0.50 | 0.50 | 0.50 |
| Citric Acid, anhydrous USP | 0.20 | 0.20 | — | 0.10 | 0.10 | 0.10 | 0.10 |
| Trisodium Citrate, dihydrate USP | 0.05 | 0.05 | — | 0.25 | 0.20 | 0.20 | 0.20 |
| Sodium Phosphate, Monobasic, Monohydrate | — | — | 0.20 | — | — | — | — |
| Sodium Phosphate, Dibasic | — | — | 0.15 | — | — | — | — |
| Grape Flavor | 0.30 | 0.30 | 0.30 | 0.30 | 0.30 | 0.30 | 0.30 |
| Propylene Glycol USP | 5.00 | 5.00 | 10.00 | 5.00 | 5.00 | 5.00 | 5.00 |
| Glycerin USP | — | — | — | — | 20.0 | 20.0 | 20.0 |
| Sucralose MP NF | 0.01 | 0.01 | 0.01 | 0.01 | 0.07 | 0.07 | 0.07 |
| Sodium Benzoate NF | 0.30 | 0.30 | — | 0.30 | 0.375 | 0.375 | 0.375 |
| Methylparaben NF | — | — | 0.15 | — | — | — | — |
| Propylparaben NF | — | — | 0.05 | — | — | — | — |
| pH (initial) | 4.0 | 4.4 | 6.5 | 5.0 | — | — | — |
| 5N HCl | q.s. | — | — | — | — | — | — |
| 2.5N NaOH | — | q.s. | q.s. | — | — | — | — |
| pH (final) | 3.1 | 5.1 | 7.1 | 5.1 | 5.1 | 5.0 | 5.1 |
| Purified Water USP | q.s. | q.s. | q.s. | q.s. | q.s. | q.s. | q.s. |
| Batch Volume (L) | 0.5 | 0.5 | 0.5 | 1.0 | 250 | 250 | 2000 |
| Density (g/mL) | ND | ND | ND | 1.006 | 1.05 | 1.05 | 1.05 |

The Example 1 solution was prepared by adding Propylene Glycol USP, Purified Water USP, Citric Acid, anhydrous USP, Trisodium Citrate, dihydrate USP, Sucralose micronized powder ("MP") NF (which has a d90≤12 microns), Sodium Benzoate NF, Tramadol HCl USP, and Grape Flavor to a suitably sized container. The initial pH of 4.0 was adjusted to a pH of 3.05 with about 5 mL of 5 N HCl. A sufficient amount (q.s.) of Purified Water USP to about 500 mL (0.5 L) was then added. All materials readily dissolved in under 1 minute. The Example 1 solution was packaged in 10×50 mL 2 oz. white PET bottles. A taste test of the Example 1 solution showed that there was an initial bitterness with some stinging.

Tramadol HCl and sodium benzoate assays performed by HPLC analysis showed that the Example 1 solution exhibited labeled contents of 98.9% for tramadol and 98.4% for sodium benzoate. The viscosity of the Example 1 solution was determined to be 1.14 to 1.40 cP (Brookfield Viscometer DV-II Pro (LV Spindle 00/25° C./60-100 rpm). A freeze-thaw test showed no signs of precipitation.

The Example 2 solution was prepared by adding Propylene Glycol USP, Purified Water USP, Citric Acid, anhydrous USP, Trisodium Citrate, dihydrate USP, Sucralose MP NF, Sodium Benzoate NF, Tramadol HCl USP, and Grape Flavor to a suitably sized container. The initial pH of 4.4 was adjusted to 5.02 using about 1.5 mL of 2.5 N NaOH. A sufficient amount (q.s.) of Purified Water USP to about 500 mL (0.5 L) was then added. The Example 2 solution was packaged in 10×50 mL 2 oz. white PET bottles. A taste test of the Example 2 solution showed improved qualities compared to the Example 1 solution (that is, there was no initial bitterness with stinging). The taste may be improved, however.

The Example 3 solution was prepared by adding Propylene Glycol USP, Methylparaben NF, Propylparaben NF, Purified Water USP, Sodium Phosphate, Monobasic, Monohydrate, Sodium Phosphate, Dibasic, Sucralose MP NF, Tramadol HCl USP, and Grape Flavor to a suitably sized container. Parabens required 5 minutes stirring to dissolve. All other materials readily dissolved (<1 minute). A small amount of precipitate was observed after addition of Grape Flavor—an additional amount of Propylene Glycol USP (25 g) was added and the composition was heated to about 50° C. with stirring until a clear solution had formed. The initial pH of 6.5 was adjusted to 7.1 using about 1.5 mL of 2.5 N NaOH. A sufficient amount (q.s.) of Purified Water USP to about 500 mL (0.5 L) was then added. The Example 3 solution was packaged in 10×50 mL 2 oz. white PET bottles. A taste test of the Example 3 solution showed a mostly bland taste with some aftertaste.

The solutions of Examples 1-3 were evaluated for pH stability and tramadol labeled content. Specifically, samples were evaluated for the pH and tramadol labeled content at four temperatures (viz., 25° C., 40° C., 55° C., and 70° C.) over four weeks. Table 2 summarizes the results of these stability tests.

TABLE 2

Test results of tramadol hydrochloride solutions at different pH-values

| Conditions | | pH | | | % L.C. | | |
|---|---|---|---|---|---|---|---|
| Temp. | Time, w | Ex. 1 | Ex. 2 | Ex. 3 | Ex. 1 | Ex. 2 | Ex. 3 |
| — | 0 | 3.130 | 5.085 | 7.106 | 101.0 | 99.8 | 99.9 |
| 25° C. | 2 | 3.060 | 5.098 | 7.107 | 99.5 | 99.9 | 99.8 |
| 25° C. | 4 | 3.158 | 5.096 | 7.030 | 100.2 | 100.7 | 99.3 |
| 40° C. | 2 | 3.177 | 5.096 | 7.100 | 101.5 | 101.1 | 101.5 |
| 40° C. | 4 | 3.143 | 5.048 | 7.013 | 101.0 | 100.5 | 99.3 |
| 55° C. | 2 | 3.142 | 5.103 | 7.038 | 100.8 | 100.6 | 96.6 |
| 55° C. | 4 | 3.161 | 5.076 | 6.963 | 101.8 | 101.7 | 99.6 |
| 70° C. | 2 | 3.138 | 5.095 | 6.817 | 102.0 | 101.9 | 93.8 |
| 70° C. | 4 | 3.175 | 5.066 | 6.639 | 103.9 | 103.8 | 95.9 |
| % RSD | | 1.1 | 0.4 | 2.2 | 1.2 | 1.2 | 2.5 |

The results of the stability tests show that the pH values of the solutions of Exs. 1 and 2 remained relatively constant over the entire testing period (cf. % relative standard deviation (RSD) of 1.1 (Ex. 1) and 0.4 (Ex. 2). However, the pH values of the solutions of Ex. 3 showed some drift (cf. % RSD of 2.5). The percent of tramadol labeled content (% L.C.) remained relatively constant for Exs. 1 and 2, but the Ex. 3 solution showed a tendency to reduce with time— especially at 70° C. This data suggests that the Ex. 3 solution might have a limited room temperature shelf-life stability, e.g., less than 2 years. The data showed that: (i) sodium benzoate is more efficacious in an acidic environment, (ii) tramadol HCl is freely soluble at a pH of about 4.5; and (iii) tramadol hydrochloride (with a pKa of 9.8) has a pH of about 5.3. Therefore, the Ex. 2 solution was evaluated for further studies.

The Example 4 solution was prepared by adding Propylene Glycol USP and Purified Water USP (about 83% of the total solution requirement) to a suitably sized container and mixing for about 5 minutes at about 350 rpm. Next, Citric Acid, anhydrous USP, Sodium Citrate dihydrate USP, Sucralose MP NF, and Sodium Benzoate NF were added in the specified amounts and mixed for about 10 minutes at about 350 rpm. The pH was measured at this stage and then Tramadol HCl USP was added and the composition was mixed for about 10 minutes at about 350 rpm. The pH was measured and the Grape Flavor was added followed by mixing for about 5 minutes at about 350 rpm. A sufficient amount (q.s.) of Purified Water USP to about 1000 mL (1.0 L) was then added, and the pH of the solution was measured. The final pH-value was 5.14 and the density was 1.006 g/mL.

The results of a preservative challenge study suggested increasing the amount of preservative (e.g., sodium benzoate). Thus, the Example 4 solution was modified to increase the amount of preservative from 0.30% w/v to 0.375% w/v in Example 5. Additionally, the results of a taste test prompted an added amount of a taste enhancer (e.g., glycerin). Thus, the Example 4 solution was modified by introducing a sufficient amount of taste enhancer (e.g., glycerin) for better taste and mouth feel. The compositional makeup of the Examples 5, 6, and 7 solutions represent the changes made to the Example 4 solution.

One or two 10"-1 micron filters were utilized depending on batch size.

The solutions of Exs. 5, 6, and 7 were manufactured as follows: (i) add a suitable amount of Purified Water USP (e.g., about 75% to 85% of the total amount) to the main mixing tank; (ii) turn on the mixer and add Propylene Glycol USP and Glycerin USP to the main mixing tank and mix for a minimum of 5 minutes at a minimum of 350 rpm; (iii) add Sodium Benzoate NF, Citric Acid, anhydrous USP, Sodium Citrate dihydrate USP, and Sucralose MP NF to the main mixing tank and mix for a minimum of 10 minutes at a minimum of 350 rpm; (iv) add Tramadol HCl USP to the main mixing tank and mix for a minimum of 10 minutes at a minimum of 350 rpm; (v) add Grape Flavor to the main mixing tank and mix for a minimum of 5 minutes at a minimum of 350 rpm; (vi) add a sufficient amount of Purified Water USP to the main mixing tank to achieve the desired batch size and mix for a minimum of 30 minutes at a minimum of 350 rpm; (vii) install 1 micron filter(s) and recirculate the product through the filter and back into the processing tank for 5 minutes; (viii) perform in-process testing: describe color and clarity, measure density and pH (remove samples as required for in-process release testing); and (ix) transfer the solution to a tote until packaged.

The solutions were packaged in a 16 oz. (480 mL fill) white high density polyethylene bottle with child-resistant closures.

Several parameters of the packaged solutions (Ex. 6) were evaluated while storing the packaged solution at 25±2° C. and 40±5% relative humidity (RH). The packages were maintained in two orientations (either on side or upright) for the entirety of the study period, which has spanned for 24 months.

The evaluated parameters include: (i) appearance; (ii) Tramadol Hydrochloride ("THCl") Assay; (iii) Sodium Benzoate ("SB") Assay; (iv) Unspecified and Unidentified Degradants ("UU Imps."); (v) Total Degradants ("Total Imps."); (vi) pH; and (vii) Weight Loss ("Wt. Loss").

Tables 3 and 4 summarize the results of the evaluated parameters over the 24-month period, where the reporting threshold (RT) is 0.1%.

TABLE 3

Evaluation of Packaged Solutions Storage Condition:
25 ± 2° C.; 40 ± 5% RH, on side

| Test | Acceptance Criteria | Sample Age (mos.) | | | | | | |
| --- | --- | --- | --- | --- | --- | --- | --- | --- |
| | | 0 | 3 | 6 | 9 | 12 | 18 | 24 |
| Appearance | Clear liquid | CON | CON | CON | CON | CON | CON | CON |
| THCl Assay | 90.0-110.0% L.C. | 100.4 | 99.9 | 99.4 | 99.1 | 98.6 | 99.3 | 99.4 |
| SB Assay | 80.0%-110.0% | 99.6 | 99.3 | 99.0 | 98.7 | 98.5 | 99.2 | 99.2 |
| UU Imps. | ≤0.2% w/w | <RT | <RT | <RT | <RT | <RT | <RT | <RT |
| Total Imps. | <1.0% | <RT | <RT | <RT | <RT | <RT | <RT | <RT |
| pH | 4.5-5.5 | 5.1 | 5.1 | 5.1 | 5.1 | 5.1 | 5.2 | 5.1 |
| Wt. Loss | NMT 5% | N/A | 0 | 0 | 0 | 0 | 0 | 0 |

The solutions of Exs. 5 and 6 were manufactured with a Batch Volume of 250 L, which required a 300 L working capacity stainless steel tank and a portable mixer equipped with a ¾"×603/4" dimensional length shaft with a 6" propeller.

The solution of Ex. 7 was manufactured with a Batch Volume of 2000 L, which requires a 2000 L working capacity stainless steel tank equipped with a mixer rated at ¾ HP, 230V capable of 350 rpm, equipped with a ¾"×71" dimensional shaft and two 13¾" propellers.

Total impurities may include Compound A (viz., RS,SR-1-(3-methoxyphenyl)-2-(dimethylaminomethyl)cyclohexanol hydrochloride (i.e., the (±) trans-isomers)), Compound B (viz., 2-[(dimethylamino)methyl]cyclohexanone hydrochloride), [2-(3-methoxyphenyl)cyclohex-1-enyl]-N,N-dimethyl methanamine (Compound C), (1RS)-[2-(3-methoxyphenyl) cyclohex-2-enyl]-N,N-dimethyl methanamine (Compound D), and/or (1RS,2RS)-2-[(dimethylamino)methyl]-1-(3-hydroxyphenyl)cyclohexanol (Compound E). Related Compound A is controlled with a specification limit of NMT 0.20%, while Related Compound B is controlled with a specification limit of NMT 0.20%. Each of the individual unidentified impurities is controlled with a specification limit of NMT 0.1%. Total impurities are controlled with a specification limit of NMT 1.0%.

TABLE 4

Evaluation of Packaged Solutions Storage Condition:
25 ± 2° C.; 40 ± 5% RH, on side

| Test | Acceptance Criteria | Sample Age (mos.) | | | | | | |
|---|---|---|---|---|---|---|---|---|
| | | 0 | 3 | 6 | 9 | 12 | 18 | 24 |
| Appearance | Clear liquid | CON | CON | CON | CON | CON | CON | CON |
| THCl Assay | 90.0-110.0% L.C. | 100.4 | 99.9 | 99.7 | 99.5 | 98.9 | 99.4 | 99.4 |
| SB Assay | 80.0%-110.0% | 99.6 | 99.4 | 99.5 | 99.1 | 98.9 | 99.0 | 99.2 |
| UU Imps. | ≤0.2% w/w | <RT | <RT | <RT | <RT | <RT | <RT | <RT |
| Total Imps. | <1.0% | <RT | <RT | <RT | <RT | <RT | <RT | <RT |
| pH | 4.5-5.5 | 5.1 | 5.1 | 5.1 | 5.1 | 5.1 | 5.2 | 5.1 |
| Wt. Loss | NMT 5% | N/A | 0 | 0 | 0 | 0 | 0 | 0 |

The results of Tables 3-4 shows that the packaged solution exhibits a tramadol hydrochloride assay amount of at least 99.4% after a 24 month period while stored at 25±2° C. and 40±5% relative humidity. Thus, a packaged solution disclosed and claimed herein is stable for at least a 24 month period when stored at 25±2° C. and 40±5% relative humidity.

Additional parameters evaluated (associated tests and acceptance criteria) include: (i) total aerobic microbial count (USP<61>, ≤200 cfu/mL); (ii) total yeast and mold count (USP<61>, ≤20 cfu/mL); (iii) specified organism (*E. coli*) (USP<62>, Absent); (iv) specified organism *B. cepacia* (USP<62>, Absent); (v) Antimicrobial Effectiveness Testing (USP<51>, Conforms to USP for Category III Products); and (vi) Package Assessment, Label adhering; no label cracks or fading; closure tight & seal intact). The packaged solutions conform to each of the additional parameters over the entire study period.

BE Fasting Study

A bioequivalence (BE) study was designed to evaluate oral relative bioavailability study of tramadol HCl oral solution (50 mg/10 mL, Ex. 6, "Test Product" or "TP") and ULTRAM® (tramadol HCl) 50 mg tablets ("Reference Product" or "RLD"), in healthy adult human subjects under fasting condition.

The primary objective of the study was to compare the rate and extent of absorption of tramadol in the Test Product and the Reference Product in healthy adult human subjects under fasting condition. A secondary objective was to assess the safety and tolerability following oral administration of tramadol oral solution.

The study was an open label, balanced, randomized, single dose, two treatment, two period, two sequence, crossover oral relative bioavailability study of Test Product and Reference Product in healthy adult human subjects under fasting condition.

Healthy, male, adult human volunteers who were willing to participate in the study and fulfill the inclusion and exclusion criteria were selected for the study. Volunteers aged from 19-42 years with a body mass index (BMI) in the range of 19.17 and 24.79 (both inclusive, calculated as weight in kg/height in m) were selected for the study. Subjects were confined within the testing facility from at least 11 hours before drug administration to 48 hours after drug administration. Subjects were randomized to either 10 mL of Test Product (viz., 50 mg dose) or one tablet of Reference Product (viz., 50 mg dose). The subjects consumed dinner at least 10 hours prior to dosing. Table 5 summarizes the meal schedule for the subjects.

TABLE 5

Meal schedule for Fasting Study

| Day | Breakfast | Lunch | Snacks | Dinner |
|---|---|---|---|---|
| | Time post dose (hr) | | | |
| Check-in day | NA | NA | NA | At least 10 hrs prior to dosing |
| Dosing day (D) | NA | 4 | 8 | 12 |
| D + 1 day | 24 | 28 | 32 | 36 |

As per the randomization schedule, in period-I, 18 subjects received the Test Product and 18 subjects received the Reference Product and in period-II, 17 subjects received the Test Product and 16 subjects received Reference Product.

After overnight fasting of at least 10 hrs, subjects were administered a single oral dose of the Test Product (T). After subjects swallowed the Test Product, the drug-dispensing syringe was rinsed with an adequate amount of water (from the given 240 mL of water used for drug administration) for 2 to 3 times and swallowed the rinse. The remaining amount of drinking water from 240 mL was administered at room temperature in sitting position, under fasting condition.

After overnight fasting of at least 10 hours, one tablet of Reference Product along with 240 mL of drinking water was administered orally to the subjects in sitting position, at room temperature.

Drug administration was done as per the randomization schedule. Dosing for the subjects started at 08:00 hours and completed at 08:22 hours in both the periods in sitting position.

In each period, a total of 24 blood samples (1×5 mL each) in each period at each time point) and in study total 48 blood samples were collected as per the following schedule: Pre-dose (0 hour) sample within 1 hour prior to drug administration and the others at 0.25, 0.50, 0.75, 1.00, 1.25, 1.50, 1.75, 2.00, 2.25, 2.50, 2.75, 3.00, 3.50, 4.00, 5.00, 6.00, 8.00, 10.00, 12.00, 16.00, 24.00, 36.00 and 48.00 hrs post dose into 5 mL K$_2$EDTA vacutainers over ice. Once blood samples from each time point were collected, they were transferred for centrifugation at 3800 rpm for 10 minutes at 4° C.±2° C. The plasma was then be separated, transferred into two aliquots of properly labeled polypropylene tubes. The time interval between sample collection and the start of centrifugation did not exceed 30 minutes. Freeze plasma samples immediately (within 60 minutes) from the sample collection time. Plasma Samples were stored at −70° C.±15° C. until drawn for analysis. Analysis of Tramadol and O-desmethyltramadol in plasma concentration was performed by a validated LC-MS/MS analytical method.

A wash out period of at least 7 days was maintained between each consecutive drug administration to minimize the carry over effects and to eliminate the drug from the body.

Pharmacokinetic parameters of the Test Product and Reference Product were assessed. Pharmacokinetic measurements are the concentrations of the drug in the plasma over a period when the samples taken. From the time/concentration values, various Pharmacokinetic parameters Cmax, AUC0-t, AUC0-inf, Tmax, t½ and Kel for tramadol and O-desmethyltramadol were calculated and these were used in the statistical analysis to compare the relative bioavailability of the two products.

Cmax, AUC0-t and AUC0-inf for tramadol were considered as primary pharmacokinetic variables. The acceptance range for bioequivalence is 80-125% for 90% confidence intervals for the ratio of least square means of the ln-transformed primary pharmacokinetic variables.

Pharmacokinetic parameters were calculated using Phoenix® WinNonlin® Version 6.3. The Mean, Standard Deviation, Minimum, Median, Maximum and Coefficient of Variation were calculated for plasma concentrations of Tramadol and O-desmethyltramadol for each sampling time, treatment and for Cmax, AUC0-t, AUC0-inf, Tmax, t½ and Kel for tramadol and O-desmethyltramadol. The calculation of these pharmacokinetic parameters was explained below.

Cmax, the maximum observed concentration and Tmax, the time to reach that peak concentration, were determined for each subject and for each treatment.

To calculate the elimination rate constant (Kel), regression analysis was performed on the natural log (Ln) of plasma concentration values (Y-axis) versus time (X-axis). Calculations were made between a time point where log-linear elimination phase begins (TLIN) and the time at which the last concentration above the limit of quantitation (LQCT) occurred. The Kel was taken as the slope multiplied by (−1) and the apparent half-life ($t_{1/2}$) as (ln 2)/Kel.

AUC0-t was calculated using the linear trapezoidal rule.

The $AUC_{0-inf}$ was calculated as: AUC0-t+Ct/Kel, where Ct is the last observed non-zero concentration for that treatment, AUC0-t is the AUC from time zero to the time of the last non-zero concentration for that treatment, and Kel is the elimination rate constant.

The analysis of variance ("ANOVA") was performed on the ln-transformed data Cmax, AUC0-t, AUC0-inf for tramadol and O-desmethyltramadol. All statistical analyses were performed using SAS® software (version 9.4 for windows).

For all analyses, Period and Treatment effects were considered statistically significant if the probability associated with 'F' less than 0.05 and for sequence effect less than 0.10.

The 90% geometric confidence intervals for ln-transformed $C_{max}$, AUC0-t and AUC0-inf for tramadol and O-desmethyltramadol were determined.

ANOVA was estimated at alpha 0.05 on the ln-transformed PK Parameters Cmax, AUC0-t and AUC0-inf for tramadol and O-desmethyltramadol. The analysis of variance model include sequence, subject nested within sequence, period and treatment as factors. The significance of the sequence effect at alpha ($\alpha$) 0.10 was tested using the subject nested within the sequence as the error term.

A total of 33 subject samples were utilized for pharmacokinetic and statistical analysis. There was no significant effect found in the study for ln-transformed pharmacokinetic parameters Cmax, AUC0-t, AUC0-inf for Tramadol.

Table 6 summarizes the pharmacokinetic ("PK") results for tramadol and O-desmethyltramadol (ODMT) observed for bioequivalence study for Test Product (TP) and Reference Product (RLD). With the exception of Tmax (reported as a median value and minimum and maximum ranges), the remaining PK values are reported as arithmetic means with corresponding standard deviations.

TABLE 6

Summary of PK Results for Tramadol and ODMT BE Fasting study

| Parameters | Tramadol | | ODMT | |
|---|---|---|---|---|
| | TP Mean ± SD | RLD Mean ± SD | TP Mean ± SD | RLD Mean ± SD |
| Tmax (hr) # | 1.5 (0.5-2.5) | 1.5 (0.75-3.00) | 2.0 (0.5-5.0) | 2.25 (1.25-10.00) |
| Cmax (ng/mL) | 180.20 ± 33.81 | 173.51 ± 29.59 | 47.77 ± 19.06 | 46.14 ± 18.28 |
| AUC0-t (hr*ng/mL) | 1623.92 ± 502.43 | 1681.64 ± 578.06 | 624.12 ± 205.58 | 624.10 ± 199.82 |
| AUC0-inf (hr*ng/mL) | 1658.31 ± 525.97 | 1721.47 ± 624.72 | 638.95 ± 207.18 | 639.26 ± 198.04 |
| t½ (hr) | 7.65 ± 1.63 | 7.61 ± 1.82 | 7.9 ± 1.6 | 8.1 ± 2.1 |
| Kel (hr−1) | 0.095 ± 0.023 | 0.096 ± 0.022 | 0.091 ± 0.019 | 0.090 ± 0.019 |

Median value for Tmax median with an associated minimum and maximum range.

One may determine the coefficient of variation (or relative standard deviation), defined as the ratio of the standard deviation (SD) to the arithmetic mean (mean), to determine the extent of variability in relation to the mean of the sample population.

Least squares geometric means, ratio of means, and 90% geometric confidence intervals were also determined for the Test Product (TP) and Reference Product (RLD), the results of which are presented in Table 7.

TABLE 7

Least squares geometric means, ratio of means, and 90% geometric confidence intervals of tramadol and ODMT for TP and RLD

|  | PK-value | TP | RLD | Ratio, % | 90% C.I. |
|---|---|---|---|---|---|
| Tramadol | AUC0-t (hr*ng/mL) | 1553.79 | 1609.16 | 96.56 | 93.62-99.59 |
|  | AUC0-inf (hr*ng/mL) | 1584.24 | 1641.66 | 96.50 | 93.51-99.59 |
|  | Cmax (ng/mL) | 177.46 | 171.35 | 103.56 | 98.68-108.70 |
| ODMT | AUC0-t (hr*ng/mL) | 578.40 | 580.08 | 99.71 | 96.84-102.66 |
|  | AUC0-inf (hr*ng/mL) | 594.09 | 597.87 | 99.37 | 96.41-102.42 |
|  | Cmax (ng/mL) | 42.75 | 40.99 | 104.29 | 99.70-109.08 |

As related to Cmax for tramadol, the Test/Reference ratio of geometric means was 103.56% and the 90% confidence interval for the ratios of the ln-transformed means was found to be 98.68-108.70%. The confidence interval was within the acceptance limits of 80-125% required for the conclusion of bioequivalence.

As related to Cmax for ODMT, the Test/Reference ratio of geometric means was 104.29% and the 90% confidence interval for the ratios of the ln-transformed means was found to be 99.70-109.08. The confidence interval was within the acceptance limits of 80-125%.

As related to AUC0-t for tramadol, the Test/Reference ratio of geometric means was 96.56% and the 90% confidence interval for the ratios of the ln-transformed means was found to be 93.62-99.59%. The confidence interval was within the acceptance limits of 80-125% required for the conclusion of bioequivalence.

As related to AUC0-t for ODMT, the Test/Reference ratio of geometric means was 99.71% and the 90% confidence interval for the ratios of the ln-transformed means was found to be 96.84-102.66%. The confidence interval was within the acceptance limits of 80-125%.

As related to AUC0-inf for tramadol, the Test/Reference ratio of geometric means was 96.50% and the 90% confidence interval for the ratios of the ln-transformed means was found to be 93.51-99.59%. The confidence interval was within the acceptance limits of 80-125% required for the conclusion of bioequivalence.

As related to AUC0-inf for ODMT, the Test/Reference ratio of geometric means was 99.37% and the 90% confidence interval for the ratios of the ln-transformed means was found to be 96.41-102.42. The confidence interval was within the acceptance limits of 80-125%.

Food Effect and Fed Bioequivalence Study

An open label, balanced, randomized, single dose, three treatment, three period, three sequence, crossover, oral food effect and fed Bioequivalence study of Tramadol HCl oral solution (50 mg/10 mL, Ex. 7) and ULTRAM® tramadol HCl) 50 mg tablets in healthy adult human subjects.

Volunteers aged from 24-42 years with a body mass index (BMI) in the range of 20.68 and 24.66 (both inclusive, calculated as weight in kg/height in m) were selected for the study.

The study included two primary objectives: (1) to evaluate the effect of food on the rate and extent of absorption of Tramadol HCl oral solution (50 mg/10 mL) in healthy adult human subjects and (2) to compare the rate and extent of absorption of Tramadol HCl oral solution (50 mg/10 mL) and ULTRAM® (tramadol HCl) 50 mg tablets in healthy adult human subjects under fed condition. A secondary objective was to assess the safety and tolerability following oral administration of Tramadol HCl oral solution.

No adverse effects were reported during the study period.

An open label, balanced, randomized, single dose, three treatment, three period, three sequence, crossover, oral food effect and fed Bioequivalence study in healthy adult human subjects. Subjects underwent screening evaluation to determine eligibility within 28 days prior to the check in of 1st period. Subjects were confined within the facility from at least 11 hours before drug administration to 48 hours after drug administration. Subjects were randomized to either 'ABC' or 'BCA or CAB' (where A=Test Product under fed condition, B=Test Product under fasting condition and C=Reference Product under fed condition) and were dosed with 240 mL of water at room temperature in sitting position.

As per the randomization schedule, in Period-I, Period-II, and Period-III, six subjects received the Test Product (A), six subjects received Test product (B), and six subjects received Reference product (C).

Treatment A administration: After overnight fasting of at least 10 hours, a high-fat high-calorie non vegetarian breakfast was served about 30 minutes prior to administration of Tramadol HCl oral solution (50 mg/10 mL). The Test Product was administered 30 minutes after start of the high-fat high-calorie non vegetarian breakfast. 10 mL of Test Product was administered orally to the subjects in a sitting position with 240 mL of water, at ambient temperature in each period as per the randomization schedule.

Treatment B administration: After overnight fasting of at least 10.00 hours, 10 mL of Test Product was administered orally to the subjects in sitting position with 240 mL of water, at ambient temperature in each period as per the randomization schedule.

After subjects swallowed the Test Product, the drug-dispensing container (syringe) was rinsed with an adequate amount of water (from the given 240 mL of water used for drug administration) for 2 to 3 times and swallow the rinse. The remaining amount of drinking water from 240 mL was administered at room temperature in a sitting position.

Treatment C administration: After overnight fasting of at least 10 hours, a high-fat high-calorie non vegetarian breakfast was served about 30 minutes prior to administration of one tablet of Reference Product, which was administered orally to the subjects in a sitting position with 240 mL of water, at ambient temperature in each period as per the randomization schedule. Subjects were instructed not to chew or crush the tablet (Reference Product) and swallow as a whole. Compliance for dosing were assessed by a thorough check of the oral cavity immediately after dosing.

Table 8 summarizes the meal schedule for the subjects of the fed/fasting study.

TABLE 8

Meal schedule for Fed/Fasting Study

| Day | Breakfast | Lunch | Snacks | Dinner |
| --- | --- | --- | --- | --- |
|  |  | Time post dose (hr) |  |  |
| Check-in day | NA | NA | NA | At least 10 hrs prior to dosing |
| Dosing day (D) | A (Yes)/B (No)/C(Yes) | 4 | 8 | 12 |
| D + 1 day | 24 | 28 | 32 | 36 |

Blood samples were taken as described above. Pharmacokinetic measurements are the concentrations of the drug in the plasma over a period when the samples taken. From the time/concentration values, various PK parameters Cmax, AUC0-t, AUC0-inf, Tmax, t½ and Kel. Tramadol and O-desmethyltramadol were calculated and these were used in the statistical analysis to compare the relative bioavailability and food effect of the two products, as explained above.

Table 9 summarizes the PK results for tramadol and O-desmethyltramadol observed for Treatment A (viz., tramadol hydrochloride oral solution (50 mg/10 mL) administered under fed conditions) and Treatment C (viz., ULTRAM® (tramadol HCl, tablets, 50 mg) administered under fed conditions). With the exception of Tmax (reported as a median value and minimum and maximum ranges), the remaining PK values are reported as arithmetic means with corresponding standard deviations.

TABLE 9

Summary of PK Results for Treatment A and Treatment C under Fed Conditions

|  | Tramadol | | ODMT | |
| --- | --- | --- | --- | --- |
| Parameters | A Mean ± SD | C Mean ± SD | A Mean ± SD | C Mean ± SD |
| Tmax (hr) # | 2.0 (0.5-3.5) | 1.9 (0.75-4.00) | 3.50 (1.75-5.00) | 2.13 (1.00-5.00) |
| Cmax (ng/mL) | 146.22 ± 28.50 | 186.63 ± 32.87 | 41.35 ± 11.53 | 44.79 ± 14.05 |
| AUC0-t (hr*ng/mL) | 1606.04 ± 574.38 | 1650.63 ± 514.55 | 623.14 ± 167.54 | 626.76 ± 143.85 |
| AUC0-inf (hr*ng/mL) | 1635.90 ± 594.44 | 1681.64 ± 536.06 | 635.05 ± 169.97 | 639.90 ± 145.57 |
| t½ (hr) | 7.33 ± 1.19 | 7.42 ± 1.42 | 7.6 ± 1.1 | 7.7 ± 1.2 |
| Kel (hr−1) | 0.097 ± 0.015 | 0.097 ± 0.020 | 0.094 ± 0.014 | 0.092 ± 0.014 |

Median value for Tmax median with an associated minimum and maximum range.

Least squares geometric means, ratio of means, and 90% geometric confidence intervals were also determined for the Test Product (T) and Reference Product (R), N=18, the results of which are presented in Table 10.

TABLE 10

Least squares geometric means, ratio of means, and 90% geometric confidence intervals based on tramadol and ODMT for Treatment A and Treatment C

|  | PK-value | A | C | Ratio, % | 90% C.I. |
| --- | --- | --- | --- | --- | --- |
| Tramadol | AUC0-t (hr*ng/mL) | 1515.80 | 1580.46 | 95.91 | 92.49-99.45 |
|  | AUC0-inf (hr*ng/mL) | 1541.65 | 1607.66 | 95.89 | 92.41-99.51 |
|  | Cmax (ng/mL) | 143.62 | 183.86 | 78.12 | 73.25-83.31 |

TABLE 10-continued

Least squares geometric means, ratio of means, and 90% geometric confidence intervals based on tramadol and ODMT for Treatment A and Treatment C

| | PK-value | A | C | Ratio, % | 90% C.I. |
|---|---|---|---|---|---|
| ODMT | AUC0-t (hr*ng/mL) | 601.08 | 609.96 | 98.54 | 94.43-102.84 |
| | AUC0-inf (hr*ng/mL) | 612.89 | 623.17 | 98.35 | 94.34-102.53 |
| | Cmax (ng/mL) | 39.54 | 42.77 | 92.47 | 87.22-98.03 |

As related to AUC0-t for tramadol, the Test (A)/Reference (C) ratio of geometric means was 95.91% and the 90% confidence interval for the ratios of the ln-transformed means was found to be 92.49-99.45%. And for ODMT, the Test (A)/Reference (C) ratio of geometric means was 98.54% and the 90% confidence interval for the ratios of the ln-transformed means was found to be 94.43-102.84%.

As related to AUC0-inf for tramadol, the Test (A)/Reference (C) ratio of geometric means was 95.89% and the 90% confidence interval for the ratios of the ln-transformed means was found to be 92.41-99.51%. And for ODMT, the Test (A)/Reference (C) ratio of geometric means was 98.35% and the 90% confidence interval for the ratios of the ln-transformed means was found to be 94.34-102.53%.

As related to Cmax, the Test (A)/Reference (C) ratio of geometric means was 78.12% and the 90% confidence interval for the ratios of the ln-transformed means was found to be 73.25-83.31% of Tramadol. The Cmax data for ODMT are dissimilar from the Tramadol results and are supportive of bioequivalence between the Test Product (A) and Reference Product (C) under fed conditions.

Table 11 summarizes the PK results for tramadol and O-desmethyltramadol observed for Treatment A (viz., tramadol hydrochloride oral solution (50 mg/10 mL) under fed conditions) and Treatment B (viz., tramadol hydrochloride oral solution (50 mg/10 mL) under fasted conditions). With the exception of Tmax (reported as a median value and minimum and maximum ranges), the remaining PK values are reported as arithmetic means with corresponding standard deviations.

TABLE 11

Summary of PK Results for the Treatment A (fed) and Treatment B (fasted)

| | Tramadol | | ODMT | |
|---|---|---|---|---|
| Parameters | A<br>Mean ± SD | B<br>Mean ± SD | A<br>Mean ± SD | B<br>Mean ± SD |
| Tmax (hr) # | 2.0 (0.5-3.5) | 1.9 (0.75-3.00) | 3.50 (1.75-5.00) | 2.00 (0.75-3.50) |
| Cmax (ng/mL) | 146.22 ± 28.50 | 160.15 ± 34.10 | 41.35 ± 11.53 | 45.66 ± 13.95 |
| AUC0-t (hr*ng/mL) | 1606.04 ± 574.38 | 1577.24 ± 585.27 | 623.14 ± 167.54 | 635.30 ± 181.16 |
| AUC0-inf (hr*ng/mL) | 1635.90 ± 594.44 | 1610.43 ± 616.17 | 635.05 ± 169.97 | 648.10 ± 181.52 |
| t½ (hr) | 7.33 ± 1.19 | 7.68 ± 1.51 | 7.6 ± 1.1 | 8.0 ± 1.5 |
| Kel (hr−1) | 0.097 ± 0.015 | 0.093 ± 0.017 | 0.094 ± 0.014 | 0.089 ± 0.015 |

Median value for Tmax median with an associated minimum and maximum range.

Least squares geometric means, ratio of means, and 90% geometric confidence intervals were also determined for the Test Product (T) and Reference Product (R), N=18, the results of which are presented in Table 12.

TABLE 12

Least squares geometric means, ratio of means, and 90% geometric confidence intervals based on tramadol and ODMT for Treatment A and Treatment B (Food Effect)

|  | PK-value | A | B | Ratio, % | 90% C.I. |
|---|---|---|---|---|---|
| Tramadol | AUC0-t (hr*ng/mL) | 1515.80 | 1484.1442 | 102.13 | 98.49-105.91 |
|  | AUC0-inf (hr*ng/mL) | 1541.65 | 1510.5231 | 102.06 | 98.36-105.91 |
|  | Cmax (ng/mL) | 143.62 | 156.7631 | 91.62 | 85.91-97.71 |
| ODMT | AUC0-t (hr*ng/mL) | 601.08 | 607.18 | 99.00 | 94.86-103.31 |
|  | AUC0-inf (hr*ng/mL) | 612.89 | 620.71 | 98.74 | 94.72-102.94 |
|  | Cmax (ng/mL) | 39.54 | 43.06 | 91.83 | 86.62-97.35 |

As related to the AUC0-t for tramadol, the Test (A)/Test (B) ratio of geometric means was 102.13% and the 90% confidence interval for the ratios of the ln-transformed means was found to be 98.49-105.91%. And for ODMT, the Test (A)/Test (B) ratio of geometric means was 99.00% and the 90% confidence interval for the ratios of the ln-transformed means was found to be 94.86-103.31%.

As related to the AUC0-inf for tramadol, the Test (A)/Test (B) ratio of geometric means was 102.06% and the 90% confidence interval for the ratios of the ln-transformed means was found to be 98.36-105.91%. And for ODMT, the Test (A)/Test (B) ratio of geometric means was 98.74% and the 90% confidence interval for the ratios of the ln-transformed means was found to be 94.72-102.94%.

As related to Cmax for tramadol, the Test (A)/Test (B) ratio of geometric means was 91.62% and the 90% confidence interval for the ratios of the ln-transformed means was found to be 85.91-97.71%. And for ODMT, the Test (A)/Test (B) ratio of geometric means was 91.83% and the 90% confidence interval for the ratios of the ln-transformed means was found to be 86.62-97.35%.

Based on the Food Effect results summarized in Table 12, it is concluded that the Test Product (A) administered under fed condition is bioequivalent to the Test Product (B) administered in fasting condition. Accordingly, a food effect was not observed with the consumption of a high-fat, high calorie meal. The data of ODMT were comparable and also demonstrate no food effect with consumption of a high-fat, high calorie meal.

CITED REFERENCES

The references cited herein are incorporated by reference in their entirety to the extent necessary. In the event that there is a difference in meaning between the incorporated terms and the terms disclosed herein and the terms of the related application, the meaning of the terms disclosed herein will control.

Alternative embodiments, examples, and modifications which would still be encompassed by the disclosure may be made by those skilled in the art, particularly in light of the foregoing teachings. Further, it should be understood that the terminology used to describe the disclosure is intended to be in the nature of words of description rather than of limitation.

Those skilled in the art will also appreciate that various adaptations and modifications of the preferred and alternative embodiments described above can be configured without departing from the scope and spirit of the disclosure. Therefore, it is to be understood that, within the scope of the embodiments described herein, the disclosure may be practiced other than as specifically described herein.

The invention claimed is:

1. An aqueous oral solution comprising:
   (a) from about 4.5 mg/mL to about 5.5 mg/mL of tramadol hydrochloride as the sole active ingredient;
   (b) from about 4% w/v to about 10% w/v of propylene glycol;
   (c) from about 10% w/v to about 30% w/v of glycerin;
   (d) a sufficient amount of a buffer to maintain the pH of the oral solution from about 4.5 to about 5.5;
   (e) from about 0.01% w/v to about 0.2% w/v sucralose;
   (f) a flavoring agent in an amount of from about 0.1% w/v to about 5% w/v;
   (g) sodium benzoate in an amount of from about 0.1% w/v to about 1% w/v; and
   (h) water,
   wherein the solution is free or substantially free of polyethylene glycol.

2. An aqueous oral solution comprising:
   (a) about 5 mg/mL of tramadol hydrochloride as the sole active ingredient;
   (b) about 5% w/v of propylene glycol;
   (c) about 20% w/v of glycerin;
   (d) about 0.1% w/v of citric acid and about 0.2% w/v of trisodium citrate dihydrate;
   (e) about 0.07% w/v of sucralose;
   (f) a flavoring agent in an amount of from about 0.1% w/v to about 1% w/v;
   (g) about 0.375% w/v of sodium benzoate; and
   (h) water,
   wherein (i) the solution has a pH of from about 4.5 to about 5.5 and (ii) the solution is free of polyethylene glycol.

3. The aqueous oral solution of claim 1, wherein the solution has a pH of from about 4.8 to about 5.4.

4. The aqueous oral solution of claim 1, wherein the solution has a pH of 5.0 or 5.1.

5. The aqueous oral solution of claim 2, wherein the solution has a pH of from about 4.8 to about 5.4.

6. The aqueous oral solution of claim 2, wherein the solution has a pH of 5.0 or 5.1.

7. The aqueous oral solution of claim 1, wherein the amount of tramadol hydrochloride is about 5 mg/mL.

8. The aqueous oral solution of claim 1, wherein the amount of propylene glycol ranges from about 5% w/v to about 7% w/v.

9. The aqueous oral solution of claim 1, wherein the buffer is a citrate buffer.

10. The aqueous oral solution of claim 9, wherein the citrate buffer is present in an amount of from about 0.2% w/v to about 0.4% w/v.

11. The aqueous oral solution of claim 1, wherein the sucralose is present in an amount of about 0.1% w/v.

12. The aqueous oral solution of claim 1, wherein the flavoring agent is grape flavor and present in an amount of from about 0.2% w/v to about 0.4% w/v.

13. The aqueous oral solution of claim 1, wherein the sodium benzoate is present in an amount of from about 0.3% w/v to about 0.4% w/v.

14. The aqueous oral solution of claim 1, wherein the solution exhibits an amount of tramadol hydrochloride of from about 0.45% w/v to about 0.55% w/v after storage at 25±2° C. and 40±5% relative humidity for 24 months.

15. The aqueous oral solution of claim 1, wherein the solution exhibits an amount of tramadol hydrochloride of from about 0.48% w/v to about 0.53% w/v after storage at 25±2° C. and 40±5% relative humidity for 24 months.

16. The aqueous oral solution of claim 1, wherein the solution exhibits an amount of tramadol hydrochloride of from about 0.49% w/v to about 0.51% w/v after storage at 25±2° C. and 40±5% relative humidity for 24 months.

17. The aqueous oral solution of claim 1, wherein the solution exhibits a tramadol maximum plasma concentration ($C_{max}$) of from about 120 ng/mL to about 220 ng/mL and an 0-desmethyltramadol $C_{max}$ of from about 24 ng/mL to about 70 ng/mL following administration of the solution to an adult human under fasted conditions.

18. The aqueous oral solution of claim 1, wherein the solution exhibits a tramadol area under the curve in a plot of analyte concentration in blood plasma versus time from zero to infinity ($AUC_{0-inf}$) of from about 825 hr*ng/mL to about 2445 hr*ng/mL and an 0-desmethyltramadol $AUC_{0-inf}$ of from about 370 hr*ng/mL to about 920 hr*ng/mL following administration of the solution to an adult human under fasted conditions; and wherein the solution is bioequivalent to an immediate release composition comprising tramadol when administered to an adult human under fasted conditions.

19. The aqueous oral solution of claim 1, wherein the solution is free or substantially free of non-ionic surfactants and/or co-solvents.

20. A method of treating pain in a subject in need thereof, which comprises administering to the subject an effective amount of the aqueous oral solution of claim 1.

* * * * *